(12) United States Patent
Genet et al.

(10) Patent No.: US 7,336,990 B2
(45) Date of Patent: Feb. 26, 2008

(54) EQUIPMENT FOR SUBSURFACE AUTOFLUORESCENCE SPECTROSCOPY

(75) Inventors: Magalie Genet, Paris (FR); Geneviève Bourg-Heckly, Paris (FR); Sandrine Vilette, Paris (FR); François Lacombe, Chaville (FR); Alexandre Loiseau, Paris (FR); Benjamin Abrat, Paris (FR)

(73) Assignee: Mauna Kea Technologies, Paris (FR)

( * ) Notice: Subject to any disclaimer, the term of this patent is extended or adjusted under 35 U.S.C. 154(b) by 63 days.

(21) Appl. No.: 10/500,162

(22) PCT Filed: Dec. 20, 2002

(86) PCT No.: PCT/FR02/04480

§ 371 (c)(1),
(2), (4) Date: Jun. 25, 2004

(87) PCT Pub. No.: WO03/060493

PCT Pub. Date: Jul. 24, 2003

(65) Prior Publication Data

US 2005/0018185 A1 Jan. 27, 2005

(30) Foreign Application Priority Data

Dec. 28, 2001 (FR) ................................. 01 16981

(51) Int. Cl.
*A61B 6/00* (2006.01)

(52) U.S. Cl. .................................... 600/477; 385/117
(58) Field of Classification Search ........ 600/473–478; 385/115–117
See application file for complete search history.

(56) References Cited

U.S. PATENT DOCUMENTS 5,813,987 A * 9/1998 Modell et al. ............... 600/473
6,470,124 B1 * 10/2002 Le Gargasson et al. ..... 385/117
6,516,217 B1 * 2/2003 Tsujita ......................... 600/477

\* cited by examiner

*Primary Examiner*—Brian L. Casler
*Assistant Examiner*—John F. Ramirez
(74) *Attorney, Agent, or Firm*—Young & Thompson

(57) ABSTRACT

An equipment includes an excitation source (1), elements for injecting (2) an excitation signal produced by the source in an ordered bundle (3) of flexible optical fibers, elements for analyzing (21, 22) an emitted autofluorescence signal. The equipment also includes at the output of the optical fiber bundle (3) an optical head (4) designed to be placed in contact with the biological tissue (6), the optical head being equipped with optical elements adapted to cause the excitation signal output from the bundle (3) to converge into a subsurface analyzing zone (5), the same optical fiber(s) used for excitation of the bundle (3) being used for detecting the signal emitted by the subsurface analyzing zone, elements (D) placed upstream of the injection elements (2) being further provided to separate the wavelength of the excitation signal and the wavelength of the autofluorescence signal.

20 Claims, 3 Drawing Sheets

FIG_1

FIG_2

EQUIPMENT FOR SUBSURFACE AUTOFLUORESCENCE SPECTROSCOPY

BACKGROUND OF THE INVENTION

The present invention relates to an equipment for subsurface autofluorescence spectroscopy. More particularly, the equipment according to the invention is of the type using an excitation signal carried by one or more flexible optical fibres.

DESCRIPTION OF THE RELATED ART

The fields of application of the invention are in-vivo spectroscopic biological tissue analysis, on humans or animals, external or internal and accessible using the instrument channel of an endoscope into which the optical fibres can be introduced, and also the ex-vivo analysis of tissue samples from biopsies, and the in-vitro analysis of cultures in cell biology.

At present the medical fields of gastroenterology, respirology, gynaecology, urology, otorhinolaryngology, dermatology, ophthalmology, cardiology and neurology are concerned.

Biological tissues contain endogenous fluorophores capable, in response to a luminous excitation of appropriate wavelength, of emitting a fluorescence in a spectral range from close to the UV to the visible, called autofluorescence. The latter results from the recovery of emissions from different fluorophores, and depends on the cell metabolism, structure and vascularization of the tissues, which vary depending on the healthy or tumorous nature of the tissues. As a result the fluorescences from healthy and tumorous tissues have strong differences with respect to both the intensity emitted and the form of the spectrum. Analysis of the autofluorescence spectrum provides indicators allowing an "optical biopsy".

In existing equipments, the illumination of the site to be spectroscopically analyzed is commonly carried out with an excitation optical fibre bundle which is divergent, exciting a volume, and the reception of the fluorescence signal is carried out by means of adjacent, in particular peripheral, detection fibres. This leads to a poor resolution, with a mixture of information and an increase in the number of false positives.

The present invention aims to overcome these drawbacks.

Moreover confocal imaging techniques with high spatial resolution have been proposed, intended for observing a section plane XY at different depths of the observed site, in particular disclosed in the Patent Application WO OO/16151.

These techniques use an organized bundle of flexible optical fibres (in particular several tens of thousands) with, on the observer's side, a light source and a system for injecting fibres allowing illumination of a single fibre and, on the side of the observed site, an optical head allowing focussing of the beam leaving the illuminated fibre into a point situated in a section plane XY, at a given depth of the observed site. A fibre scanning system allows scanning of the fibres one by one at very high speed. Each fibre is used alternately for carrying the illumination beam and also used for the corresponding return beam originating from the observed site. The obtaining of a high spatial resolution is due to the fact that the beam is focussed into a point and also to the confocal character residing in the spatial filtering of the observed site by the same fibres as those having served for the illumination. This makes it possible to receive exclusively the signal originating from the observed site and to produce an image point by point.

SUMMARY OF THE INVENTION

The present invention aims to propose equipment which allows a spectroscopic analysis also with high spatial resolution and at a given depth of the observed site.

It proposes equipment for spectroscopic analysis of autofluorescence of a biological tissue comprising an excitation source, a bundle constituted by a single flexible optical fibre or a plurality of flexible optical fibres and means for injecting an excitation signal produced by said source into said bundle according to a useful diameter corresponding to the excitation of the single fibre, all the optical fibres in the bundle or a specific sub-group, and a means for analyzing an emitted autofluorescence signal, characterized in that it comprises at the output of said flexible optical fibre bundle an optical head intended to be placed in contact with the biological tissue, said optical head being equipped with optical means adapted for converging the excitation signal coming out of said flexible optical fibre bundle into a subsurface analysis zone, the same optical fibre or fibres of said bundle having served for the excitation being used for detecting the signal emitted by said subsurface analysis zone, means placed upstream of the means for injecting being moreover provided for separating the excitation signal wavelength and the emitted autofluorescence signal wavelength.

The present invention is thus based on certain of the means mentioned above for producing a confocal image, namely carrying on the same fibres or fibres the excitation signal and the emitted return signal, and the use of an optical head focussing the excitation signal into a point at a depth. The focussing combined with the confocal character (obtained thanks to the return of the autofluorescence signal by the same optical fibre or fibres), makes it possible to obtain a high spatial resolution. The advantage compared with wide field spectroscopy is that a very precise spatial selection of the analysis zone can be carried out and the likelihood of errors and false positives is thus greatly reduced.

The optical means of the optical head comprise a system of lenses forming a focussing objective adapted for transcribing the spatial distribution of the focal spot at the fibre bundle output and for transcribing the quality of the wave front, and adapted for minimizing the parasitic reflection occurring at the fibre bundle output.

According to the present invention, the number of optical fibres in the bundle can vary between a single fibre and a plurality of fibres (in particular several tens of thousands) being able to be excited all together or by sub-groups selected according to the dimensions of the excitation zone sought.

The excitation zone according to the invention is situated in a plane XY perpendicular to the optical axis which can be adjusted to different depths, ranging approximately from 50 to 400 µm. Its dimension depends on the diameter of all of fibres used (hereafter called the useful diameter of the fibre bundle), and the optical focussing characteristics of the optical head. When a bundle constituted by a multitude of flexible optical fibres is used, the equipment can advantageously comprise means allowing adjustment of the diameter of the excitation beam emitted by the source so that it continuously excites either all of the fibres or a sub-group of fibres making it possible to obtain an appropriate size for the excitation zone. These means are for example constituted by a beam adaptation lens or an afocal system with appropriate magnification.

The present invention also proposes equipment comprising moreover means making it possible to jointly obtain a confocal image of the analysis site. Such a coupling possibility makes it possible to advantageously increase the degree of certainty of a diagnosis. Thanks to the invention, it is possible to obtain simultaneously and in real time, relative to a focussed point at a depth, information:

of histological type by confocal imaging; and of spectroscopic type concerning the nature of the observed site.

It proposes equipment as defined above, the fibre bundle comprising a plurality of optical fibres, characterized in that it comprises moreover means for jointly producing a confocal image of the analysis zone, comprising:

an illumination source, a detector of the return signal for analysis, a means for separating the illumination signal and said return signal, means for coupling the excitation signal for the spectroscopic analysis and the illumination signal for the confocal imaging, before introduction into the means for injecting into the optical fibre bundle, a means for rapid scanning of the fibres one by one situated upstream of the means for injecting into the fibre bundle, and a spatial filtering system at the signal detector input adapted for selecting the return signal originating from the illuminated fibre, the means for injecting into the fibre bundle having a spatial distribution of the focal spot intensity equal to the diameter of a fibre core, each fibre being illuminated alternately and in an addressed manner.

According to the invention, the tomographic and spectroscopic routes advantageously share the means for injecting into the fibre bundle, the fibre bundle itself and the optical focussing head. For the acquisition of an image, the fibres are illuminated alternately and one by one. For the acquisition of an autofluorescence spectrum, the fibres can be excited all together or by sub-groups, as a function of the dimensions of the analysis zone.

The use of a flexible optical fibre bundle can be advantageous for a system of automatic tests in which advantageously the fibre bundle, with the optical head at its end, is manipulated automatically as a measuring arm on a matrix of samples.

BRIEF DESCRIPTION OF THE DRAWINGS

The present invention will be better understood and other advantages will become evident in light of the description which follows of two embodiments, which description refers to the drawings in which.

DESCRIPTION OF THE PREFERRED EMBODIMENTS

Figure 1:
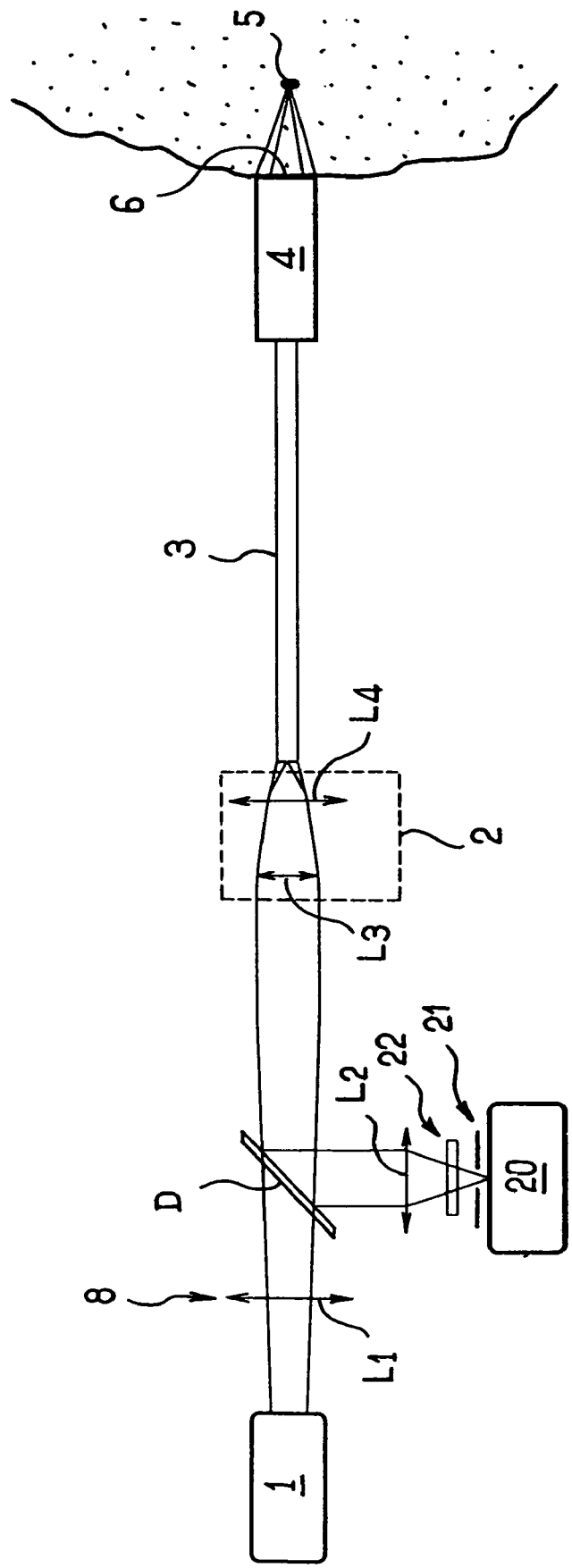
FIG. 1 illustrates diagrammatically a first embodiment of spectroscopy equipment according to the invention.

According to the embodiment chosen and represented in FIG. 1, an equipment is proposed for producing a subsurface spectroscopic analysis at a given depth, comprising a source 1 producing an excitation signal, a means for injecting 2 said signal into an organized optical fibre bundle 3 at the end of which is arranged an optical head 4 adapted for modifying the excitation signal leaving said optical fibre bundle 3 in order to create a convergent beam focussed on a zone 5 underlying the zone of contact 6 with the optical head 4.

The source 1 used is chosen in order to allow excitation of the endogenous fluorophores present in the biological tissues of the observed site, in particular in a wavelength range of 300-500 nm. Typically a 405+/−10 nm diode laser can be used. Other sources such as solid lasers or gas lasers with or without harmonic generators can also be suitable with other wavelengths in order to excite other endogenous fluorophores.

The equipment comprises a means for adapting 8 the beam emitted by the source 1 comprising here a lens L1 which is correctly coupled to the means for injecting 2 into the optical fibre bundle 3. The optical combination allows adaptation of the size of the laser beam to the useful diameter of said optical fibre bundle 3, corresponding to all or a sub-group of fibres effectively used. Moreover it makes it possible here to increase the diameter of the focal spot at the input to the fibre bundle 3 and as a result to increase the size of the spot formed on the tissue. This makes it possible to reduce the irradiance (i.e. the quantity of power per surface unit) on the tissue, and thus to respect the standards of illumination of biological tissues.

The equipment also comprises a means adapted for separating two wavelengths, the excitation wavelength and the emitted autofluorescence signal. A dichroic plate D is used here to this end achieving maximal transmission at the illumination wavelength and a maximal reflection in the fluorescence spectral range.

The signal at the excitation wavelength is directed at the output of the plate D towards the optical means for injecting 2 into the fibre bundle 3. This means should have the minimum number of aberrations and should not degrade the quality of the wave front in order to produce a focal spot close to the diffraction limit in order thus to produce an optimal coupling with the fibre bundle 3. The means chosen here is constituted by a custom-made doublet L3 and a standard triplet L4. The doublet L3 allows correction of the residual aberrations of the triplet L4, namely the curvature of field. Any other optical system having a wave front quality WFE ("Wave Front Error") of the order of $\lambda/8$ and a spatial distribution of the focal spot intensity PSF ("Point Spread Function") equal to the useful diameter of the fibre bundle 3 can be suitable.

The fibre bundle 3 allows access to the analysis zone by off-setting the source 1. For endoscopic use, it should have a diameter and a radius of curvature allowing easy insertion into the instrument channel of the endoscope, which is a few millimeters in diameter in accordance with clinical use (between 2 mm and 4 mm). It is possible to use a bundle constituted by a single flexible optical fibre or a plurality of fibres. In practice, the useful diameter can be chosen as a function of the focal spot of the optical head, for example so that it is of the order of several hundreds of microns, in which case it is known that the nature of the biological tissue observed does not differ from one cell to another.

At the fibre bundle 3 output, the excitation signal passes through the optical head 4. The latter comprises several optical means, allowing convergence of the excitation signal, and two glass plates (not represented in the figures), one shared with the fibre bundle 3 output and the other in contact with the tissue in order to produce an index adaptation with the biological tissues.

The optical means have the following characteristics:
allowing analysis of the tissue at a depth of several tens to several hundreds of microns;
minimization of the aberrations in order to transcribe the PSF at the fibre bundle output onto the tissue without enlarging the latter or deforming it;
optimization of the return coupling level in the fibre bundle by optimizing the quality of the wave front;
minimization of the parasitic reflection occurring at the fibre bundle output by the integration of a glass plate.

Moreover, if it is an optical head intended for an endoscope, its dimensions should be compatible with that of the instrument channel of the endoscope.

The optical focussing unit is constituted by a system of lenses with or without unitary magnification, forming a custom-made objective or a system comprising for example two microscope objectives.

According to the invention, the fibre or fibres of the bundle 3 also have the function of detecting the signal emitted by the subsurface zone 5. At the fibre bundle output 3, the signal detected is, as has been seen, reflected by the dichroic plate D and directed towards the slit 21 of a spectrograph 20. The coupling of the fluorescence signal to the slit 21 of the spectrograph is achieved thanks to an achromatic doublet. As a variant, any other achromatic optics can be used, the analysis of the fluorescence signal being carried out over a wide spectral range (350 nm-650 nm). A high-pass filter 22 thus allows elimination of the excitation wavelength (the light backscattered by the tissue at the same wavelength as the excitation wavelength is in fact much greater than the autofluorescence light of the tissues which is produced at higher wavelengths). As a result, in order not to saturate the detector, the light backscattered is blocked by the high-pass filter and a lens L2, placed upstream of the high-pass filter 22, allows improvement of the signal-to-noise ratio by enhancing the signal detected by adaptation of the return beam to the dimensions of the slit 21.

The spectrograph 20 is chosen in order to have a wide numerical aperture, a cooling-down by the Peltier effect, a low noise level in order to improve the signal-to-noise ratio, as well as a good spectral resolution (of the order of 3 nm). Means for displaying the spectrum, and of analyzing and processing are moreover provided.

Figure 2:
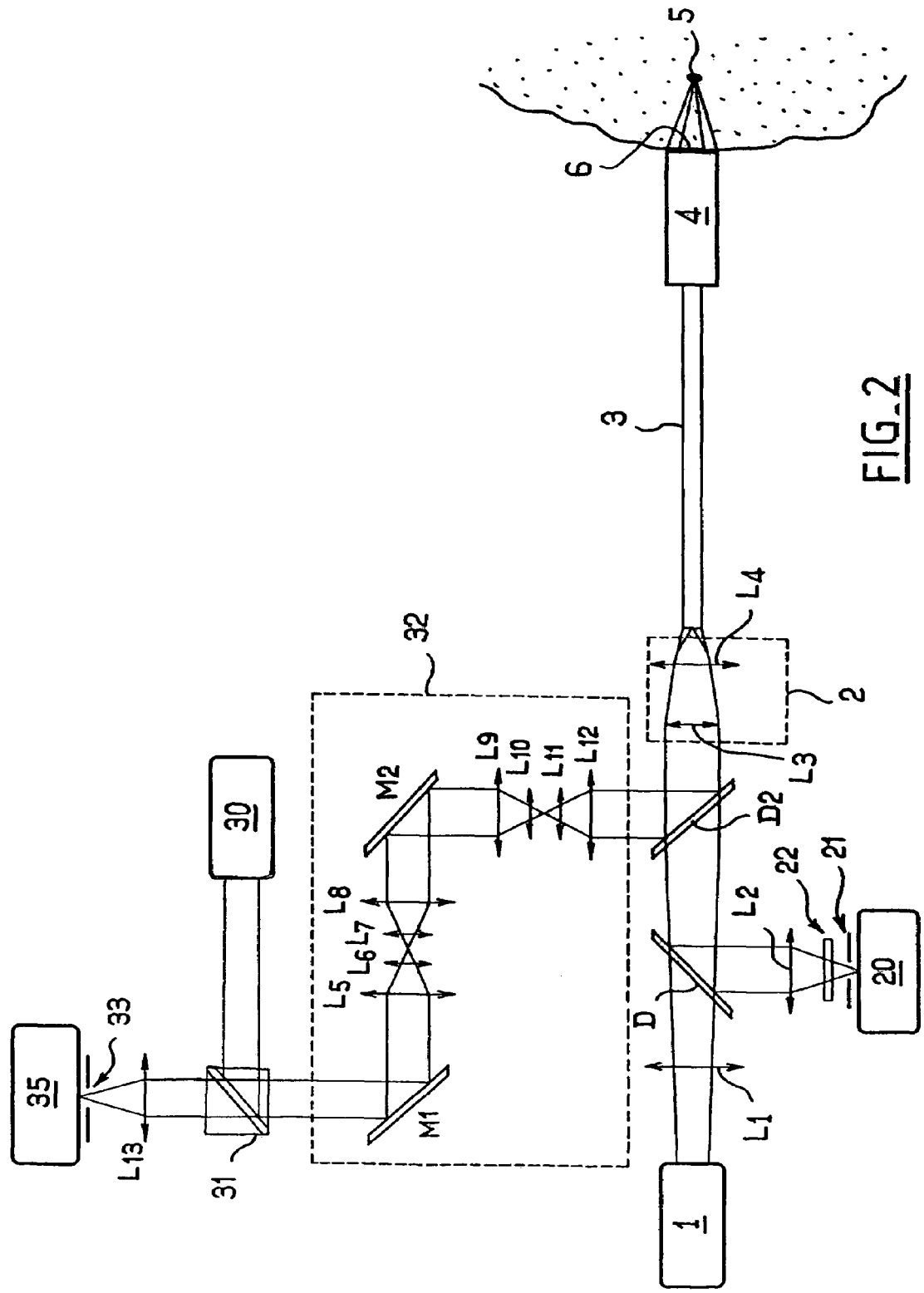
FIG. 2 illustrates diagrammatically a second embodiment of equipment comprising a spectroscopic analysis and confocal imaging coupling.

FIG. 2, shows diagrammatically the equipment of FIG. 1 to which a confocal imaging system has been advantageously coupled. The equipment therefore comprises a spectroscopic route which corresponds to that described with reference to FIG. 1 (the same references are used) and an additional tomographic route making it possible to produce in conjunction a confocal image of the analysis site. The two routes advantageously share the optical fibre bundle 3 and the optical head 4, as well as the means for injecting 2 into said fibre bundle 3.

Specifically, in order to obtain a confocal image point by point, the equipment uses here a bundle 3 comprising several optical fibres which are illuminated one by one and alternately, in an addressed manner. Any bundle having enough fibres and a small inter-core spacing can be used in order to obtain a good spatial resolution. By way of example, a Sumitomo® strand of optical fibres can be used constituted by 30,000 fibres with a core diameter of 2.5 µm and inter-core spacing of 4 µm, or a Fujikura® strand constituted by 30,000 fibres with a core diameter of 2 µm and inter-core space of 3.7 µm. Such fibre bundles are compatible with endoscopic use. For the spectroscopic route, the acquisition of the spectrum with such fibre bundles takes place over the totality of the fibres of the bundle which corresponds to an analysis zone of several hundreds of microns in which the nature of the tissue does not differ from one cell to another.

Also specifically, the optical head is adapted for confocal imaging fibre by fibre making it possible to obtain a focussed analysis zone 5 of the order of 0.5 mm in diameter in an analysis section plane XY.

Upstream of the fibre bundle 3, the tomographic route comprises a source 30 constituted by a 683 nm laser diode and having a very good wave front quality. This diode is pulsed in order to split by synchronous detection the useful signal from the parasitic reflection occurring at the input to the fibre bundle 3. A solid or gas laser could also be used, but the choice of wavelength in the 600-800 nm band where the absorption into the tissues is lower, is less extensive; Moreover, the equivalent power cost is much greater.

In order to separate the illumination signal and the return analysis signal, a means for separating is used, constituted here by a 50/50 separating cube 31 for adjustment facilities. A 50/50 separating plate can also be used.

The equipment comprises a scanning system 32 the aim of which is to reproduce a matrix of diodes of the same optical quality as the laser diode of the source and which will be injected fibre by fibre. This requires a combination of non standard optical means allowing correction of the aberrations present in the transport and source duplication system in order to illuminate the bundle 3 fibre by fibre. This point-by-point imaging technique (each point corresponding to the illumination of one fibre) makes it possible to obtain a confocal image of very good quality and at an appropriate image speed (15 images/s).

The scanning system is constituted by two mirrors M1 and M2, one is a mirror resonating at a frequency of 4 kHz or 8 kHz, the other a galvanometric mirror with a variable frequency between 0 and 300 Hz, and two optical systems each constituted by four lenses, respectively L5, L6, L7 and L8, and L9, L10, L11 and 12 allowing first conjugation of the two mirrors, then the mirror M2 and the fibre bundle 3 input. These optical systems should not have aberrations which could:
widen the PSF after the injection system and thus degrade the coupling in the fibre bundle 3;
propagate flux in the sheath which would degrade the PSF at the end of the fibre bundle 3 and therefore the resolution of the equipment.

Unlike the equipment of FIG. 1, the means for injecting 2 into the fibre bundle 3 should have here a PSF equal to the diameter of a fibre core in order to be able to produce an optimal coupling with a single fibre.

The lenses L6-L7 and L10-L11 of the scanning system 32 are two identical corrective doublets placed symmetrically relative to the image plane. They make it possible, with the doublet L3 of the system for injecting 2 to obtain an image of very good quality by eliminating the residual aberrations of the optical combination of L5, L8, L9, L12 and L4, and to uniform the coupling level in the fibre bundle 3 by eliminating the curvature of field. They also therefore make it possible to improve the spatial resolution of the equipment by forming a spot with a PSF equal to the core diameter of the fibres, which does not lead to light propagation in the sheath of the fibre bundle 3, and therefore a PSF at the output of said bundle 3 identical to that at the input.

The equipment comprises a spatial filtering system constituted by a lens L13 and a filtering hole 33 making it possible to select only the illumination fibre and not the adjacent fibres which can generate a parasitic signal. The size of the filtering hole is such that it corresponds to the diameter of a fibre core, taking into account the magnification of the optical system, between the input to the fibre bundle 3 and the filtering hole 33.

The fibre bundle 3 is equipped at both ends with a glass plate sufficiently thick and with an index sufficiently close to that of the fibres in order to reject the parasitic reflections outside the filtering hole placed in front of the detector regarding the reflection occurring at the input to the fibre bundle 3, and outside the optical fibres illuminated regarding the reflection occurring at the output of the fibre bundle 3. The glass plates have undergone anti-reflection treatment in order to minimize the light reflected.

As signal detector 35 an avalanche photodiode is used which acquires the signal continuously, which makes it necessary to carry back the parasitic signal originating from the two ends of the fibre bundle 3 with the same order of magnitude as the useful signal in order not to saturate the detector. The elimination of the parasitic reflection residue at the input of the fibre bundle 3 is then carried out by digital time filtering. Any other monopixel photodetector such as the photomultiplier can be used, the advantage of the avalanche photodiode being its quantum yield of detection which is higher than that of other detectors.

In order to proceed with the coupling of the two confocal imaging/spectroscopy routes which is carried out with two different wavelength sources, a dichroic plate D2 reflecting the red and transmitting the blue and the green is used. The coupling could also be carried out with transmission in the red and reflection in the blue and the green, but it has less optimal reflection and transmission levels in this way.

In operation, the acquisition of a spectrum can be carried out simultaneously with the acquisition of a tomographic image. The equipment comprises means for analyzing and processing which allow a digital image to be recreated from the signals detected by the signal detector 35.

The spatial resolution which can be obtained is of the order of 5 μm. It allows in particular the diagnosis of pre-cancerous lesions based on the size, form and density of the nuclei observed.

Figure 3:
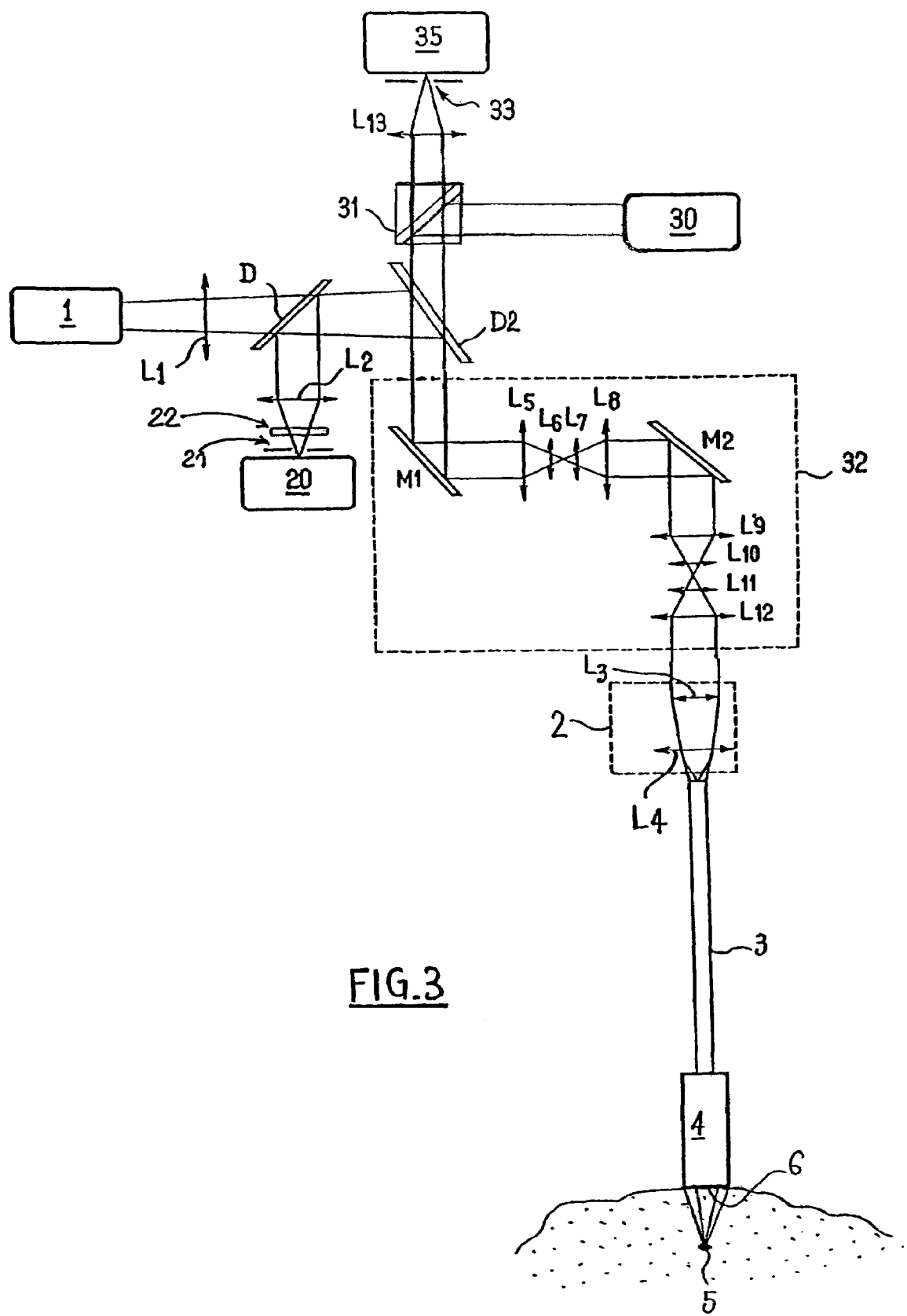
FIG. 3 illustrates diagrammatically an embodiment variant of the equipment of FIG. 2.

FIG. 3 shows an embodiment variant of the equipment of FIG. 2. The identical elements bear the same references in the two figures. According to this variant, the coupling of the two confocal imaging/spectroscopy routes is carried out upstream of the scanning means 32. To this end, the dichroic plate D2 is placed upstream of the mirror M1. The advantage of this construction is that it allows use of the scanning means 32 for displacing an excitation beam emitted on the spectroscopic route that has a smaller useful diameter than the total diameter of the fibre bundle 3, in order to inject it at a different position on the input surface of the bundle 3. This allows for example displacement of the spectroscopic analysis zone in order in particular to make it corresponds to an image zone obtained by the confocal imaging route.

As a variant also, which can be applied to the equipment of FIGS. 1 to 3, as a replacement for the adaptation lens L1, an afocal system can be provided allowing modification of the size of the excitation beam in order to make it correspond to a given sub-group of optical fibres in the bundle 3.

The invention claimed is:

1. Equipment for spectroscopic analysis of autofluorescence of a biological tissue comprising:
   an excitation source (1),
   a bundle (3) constituted by a single optical fibre or a plurality of flexible optical fibres,
   means for injecting (2) an excitation signal produced by said excitation source into said bundle according to a useful diameter corresponding to the excitation of the single fibre, all the optical fibres in the bundle or a specific sub-group, and
   a means for analyzing (21, 22) an emitted autofluorescence signal,
   an optical head (4) at said bundle (3) output,
   said optical head (4) intended to be placed in contact with the biological tissue (6),
   said optical head being equipped with optical means adapted for converging the excitation signal coming out of said bundle (3) into a subsurface analysis zone (5), the same optical fibre or fibres of said bundle having served for carrying the excitation signal being used for detecting the signal emitted by said subsurface analysis zone, and
   means (D) placed upstream of the means for injecting (2) provided for separating the excitation signal wavelength and the autofluorescence signal wavelength.

2. Equipment according to claim 1, wherein the optical means of the optical head (4) comprise a system of lenses forming a focussing objective adapted for transcribing the spatial distribution of the focal spot (PSF) at the fibre bundle output and the quality of the wave front (WFE) and for minimizing the parasitic reflection occurring at the fibre bundle output.

3. Equipment according to claim 1, wherein the optical head (4) comprises a glass plate intended to come into contact with the biological tissue to be analyzed and adapted for producing an index adaptation with said tissue.

4. Equipment according to claim 1, further comprising:
   a glass plate placed at the output of the optical fibre bundle (3) and shared with the optical head (4),
   said plate being sufficiently thick to reject the parasitic parallel reflections at the output of said fibre bundle (3).

5. Equipment according to claim 1, wherein the means for injecting (2) into the optical fibre bundle (3) has a wave front quality and a spatial distribution of the focal spot intensity adapted to the useful diameter of the fibre bundle (3).

6. Equipment according to claim 1, wherein the excitation source (1) emits at a wavelength adapted to excite chosen endogenous fluorophores present in the biological tissues of the observed site.

7. Equipment according to claim 1, wherein for separating the wavelengths is a dichroic plate (D).

8. Equipment according to claim 1, wherein the means for spectroscopic analysis comprise a spectrograph (20) and a means of coupling (21) to the slit of the spectrograph.

9. Equipment according to claim 8, wherein the means for coupling (21) to the slit of the spectrograph comprises an achromatic optical means.

10. Equipment according to claim 8, further comprising:
    a means for rejecting (22) placed upstream of the coupling means (21) and adapted for eliminating the backscattered excitation wavelength.

11. Equipment according to claim 10, further comprising:
    a lens (L2) placed upstream of the means for rejecting (22) adapted for improving the signal-to-noise ratio.

12. Equipment according to claim 1, further comprising:

a means for adapting (L1) the size of the beam emitted by the excitation source (1) to the useful diameter of the optical fibre bundle (3).

13. Equipment according to claim 1, wherein the fibre bundle (3) comprising a plurality of optical fibres, further comprises means for jointly producing a confocal image of the analysis zone (5), comprising:

an illumination source (30), a detector (35) of the return signal for analysis, a means for separating (31) the illumination signal and said return signal, means for coupling (D2) the excitation beam for the spectroscopic analysis and the illumination beam for the confocal imaging, before introduction into the means for injecting (2) into the optical fibre bundle (3), a means (32) for rapid scanning one by one of the fibres situated upstream of the means for injecting into the fibre bundle (3), and a system for spatial filtering (33) at the input to the signal detector (35) adapted for selecting the return signal originating from the fibre illuminated, the means for injecting (2) into the fibre bundle (3) having a spatial distribution of the focal spot intensity equal to the diameter of a fibre core, each fibre being illuminated alternately and in an addressed manner.

14. Equipment according to claim 13, wherein the means for coupling are placed upstream of the scanning means (32).

15. Equipment according to claim 13, wherein the illumination source (30) is a pulsed laser diode.

16. Equipment according to claim 13, wherein the illumination source has a wave front quality of the order of $\lambda/8$.

17. Equipment according to claim 13, wherein the detector (35) of the return signal is an avalanche photodiode.

18. Equipment according to claim 13, wherein the means for coupling (31) the excitation signal for the spectroscopic analysis and the illumination signal for the confocal imaging, comprise a dichroic plate (D2).

19. Equipment according to claim 13, wherein the means (32) for rapid scanning of the fibres one by one comprises a mirror (M1) resonating at a given frequency and a galvanometric mirror (M2) with a variable frequency, and two optical systems each constituted by lenses (L5-8, L9-12) first adapted for conjugating the two mirrors (M1, M2) then the galvanometric mirror (M2) and the fibre bundle (3) input.

20. Equipment according to any claim 13, wherein the spatial filtering system comprises a filtering hole (33) the size of which is such that it corresponds to the diameter of a fibre core, taking into account the magnification of the optical system, between the fibre bundle (3) input and the filtering hole (33).

* * * * *